(12) United States Patent
Shin et al.

(10) Patent No.: US 8,481,174 B2
(45) Date of Patent: Jul. 9, 2013

(54) ORGANIC LIGHT-EMITTING COMPOUND OF CIS-DIARYLETHENE DERIVATIVES, ORGANIC ELECTROLUMINESCENT DEVICE USING THE SAME, AND METHOD OF MANUFACTURING THE DEVICE

(75) Inventors: Dong-Woo Shin, Yongin-si (KR);
Woon-Jung Paek, Yongin-si (KR);
Byoung-Ki Choi, Yongin-si (KR);
O-Hyun Kwon, Yongin-si (KR);
Myeong-Suk Kim, Yongin-si (KR);
Young-Mok Son, Yongin-si (KR);
Eun-Sil Han, Yongin-si (KR); Jung-Bae Song, Yongin-si (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 1867 days.

(21) Appl. No.: 11/643,979

(22) Filed: Dec. 22, 2006

(65) Prior Publication Data

US 2007/0276160 A1 Nov. 29, 2007

(30) Foreign Application Priority Data

May 24, 2006 (KR) ........................ 10-2006-0046543

(51) Int. Cl.
*C09K 11/06* (2006.01)
*H01L 51/54* (2006.01)
*C07C 211/00* (2006.01)
*C07D 209/82* (2006.01)

(52) U.S. Cl.
USPC ........ 428/690; 428/917; 428/411.1; 548/440; 564/427; 564/428; 564/429; 257/40; 313/502

(58) Field of Classification Search
USPC ........................................................ 428/690
See application file for complete search history.

(56) References Cited

U.S. PATENT DOCUMENTS 4,356,429 A 10/1982 Tang 7,374,828 B2 * 5/2008 Kondakova et al. .......... 428/690

FOREIGN PATENT DOCUMENTS

JP 05-224442 9/1993
JP 05224442 A * 9/1993

OTHER PUBLICATIONS

Machine English translation of JP 05224442 A. Translated dec. 9, 2009.*

(Continued)

*Primary Examiner* — Jennifer A Chriss
*Assistant Examiner* — J. L. Yang
(74) *Attorney, Agent, or Firm* — Robert E. Bushnell, Esq.

(57) ABSTRACT

Provided are an organic light-emitting compound that is a diarylethene derivative represented by Formula 1, and an organic electroluminescent (EL) device using the organic light-emitting compound, and a method of manufacturing the organic EL device:

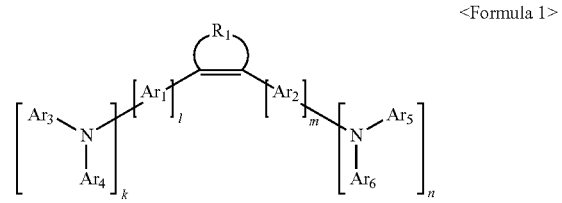

<Formula 1> where $R_1$, $Ar_1$, $Ar_2$, $Ar_3$, $Ar_4$, $Ar_5$, $Ar_6$, k, l, m, and n are the same as defined in the specification. The organic light-emitting compound contains a cis-diarylethene group linked with an aliphatic ring, and thus crystallization of the organic light-emitting compound is unlikely to occur and the compound is highly soluble to organic solvents and easily provides liquid formulation with organic solvents. Thus, the organic light-emitting compound can easily be used in organic EL devices. An organic EL device manufactured using the compound can have a thermostable layer and thus has improved light-emitting properties in term of superior turn-on voltage, efficiency, color purity, etc.

18 Claims, 3 Drawing Sheets

OTHER PUBLICATIONS

Wei-Ching Wu et al., "Red Organic Light-Emitting Diodes with a Non-doping Amorphous Red Emitter", Adv. Mater. 2002, 14, No. 15, 1072-1075, Aug. 5.

Zengqi Xie et al., "Supramolecular Interactions Induced Fluorescence in Crystal: Anomalous Emission of 2,5-Diphenyl-1,4-distyrylbenzene with All cis Double Bonds", Chem. Mater. 2005, 17, 1287-1289.

Yoshiyuki Kuwabara et al., Termally Stable Multilayered Organic Electroluminescent Devices Using Novel Starburst Moleculer, 4,4",4Δ-Tri(N-carbazolyl)triphenylamine (TCTA) and 4,4∝,4Δ-Tris(3-methylphenylphenyl-amino)triphenylamine (m-MTDATA), as Hole-Transport Materials, Adv. Mater. 1994, 6, No. 9, 677-679.

Chinese Office Action issued by Chinese Patent Office on Jan. 12, 2011, corresponding to Korean Patent Application No. 2006-0046543 and Request for Entry of the Accompanying Office Action attached herewith.

* cited by examiner

ORGANIC LIGHT-EMITTING COMPOUND OF CIS-DIARYLETHENE DERIVATIVES, ORGANIC ELECTROLUMINESCENT DEVICE USING THE SAME, AND METHOD OF MANUFACTURING THE DEVICE

CROSS-REFERENCE TO RELATED PATENT APPLICATIONS AND CLAIM OF PRIORITY

This application claims the benefit of Korean Patent Application No. 10-2006-0046543, filed on May 24, 2006, in the Korean Intellectual Property Office, the disclosure of which is incorporated herein in its entirety by reference.

BACKGROUND OF THE INVENTION

1. Field of the Invention

The present invention relates to an organic light-emitting compound, an organic electroluminescent (EL) device using the compound, and a method of manufacturing the organic EL device, and more particularly, to an organic light-emitting compound that contains a cis-diarylethene group linked with an aliphatic ring, which prevent crystallization of the organic light-emitting compound, and thus is highly soluble to organic solvents and easily provides liquid formulation with organic solvents, an organic EL device using the compound, and a method of manufacturing the organic EL device.

2. Description of the Related Art

Electroluminescent (EL) devices are self-emitting devices which have a wide viewing angle, excellent contrast, and quick response time. EL devices can be classified into inorganic EL devices which use inorganic compounds for emissive layers and organic EL devices which use organic compounds for emissive layers. Compared to inorganic EL devices, organic EL devices have superior luminance, lower turn-on voltage, and quicker response time, and can realize multicolor images.

A typical organic EL device has a stacked structure in the form of an anode/organic emissive layer/cathode structure. Organic EL devices can also have an anode/hole injection layer (HIL)/hole transport layer (HTL)/emissive layer/electron transport layer (ETL)/electron injection layer (EIL)/cathode structure, or an anode/HIL/HTL/emissive layer/hole blocking layer/ETL/EIL/cathode structure.

Materials used in organic EL devices can be classified into vacuum deposition materials and solution coating materials. Vacuum deposition materials should be able to have a vapor pressure of $10^{-6}$ torr or higher below 500° C. and may be small molecular materials having a molecular weight of 1200 or less. Solution coating materials should have sufficient solubility and typically include aromatic compounds or heterocyclic compounds.

Manufacturing organic EL devices using vacuum deposition increases costs due to the use of a vacuum system. In addition, when a shadow mask is used to define pixels for natural color display, manufacturing high-resolution pixels is difficult.

On the other hand, manufacturing organic EL devices using solution coating methods such as inkjet printing, screen printing, and spin coating is easy, costs less, and can accomplish a relatively higher resolution than using a shadow mask. However, in terms of thermostability and color purity, blue light emitting molecules which are compatible with solution coating methods are inferior to materials that are compatible with vacuum deposition methods. Also, even when the features are superior, as crystallization occurs after manufacturing, crystals which become as large as the wavelengths of visible light disperse visible light and cause white residue. In addition, pin holes are likely to be formed and deteriorate the devices.

Accordingly, efforts have been made to overcome the limits of the conventional methods and materials and provide a material and an organic EL device which have improved features. However, a satisfactory solution has not yet been obtained.

Thus, a novel small molecular material having improved solubility that is compatible with solution coating methods, and an organic EL device which can be easily manufactured and has a higher resolution using a solution coating method, and which has high thermal stability and color purity due to the use of the small molecular material, are required.

SUMMARY OF THE INVENTION

The present invention provides an organic light-emitting compound that is a diarylethene derivative having a cis-type structure.

The present invention also provides an organic EL device which is manufactured using the organic light-emitting compound.

The present invention also provides a method of manufacturing the organic EL device using the above organic light-emitting compound.

According to an aspect of the present invention, there is provided an organic light-emitting compound that is a cis-diarylethene derivative represented by Formula 1:

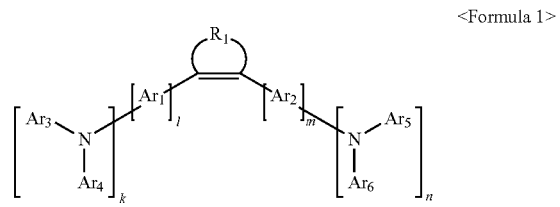

<Formula 1> where $R_1$ is a substituted or unsubstituted $C_1$-$C_{30}$alkylene group, an alkenylene group, or an alkynylene group;

$Ar_1$ and $Ar_2$ are each independently a substituted or unsubstituted $C_6$-$C_{30}$arylene group or a substituted or unsubstituted $C_2$-$C_{30}$heteroarylene group;

$Ar_3$, $Ar_4$, $Ar_5$ and $Ar_6$ are each independently a substituted or unsubstituted $C_6$-$C_{30}$aryl group, or a substituted or unsubstituted $C_2$-$C_{30}$heteroaryl group;

$Ar_3$ and $Ar_4$ can be linked to form a ring, and $Ar_5$ and $Ar_6$ can be linked to form a ring;

l and m are each independently integers from 1 to 6; and k and n are each independently integers from 0 to 6, wherein at least one of k and n is larger than or equal to 1.

According to another aspect of the present invention, there is provided an organic EL device including a first electrode, a second electrode, and an emissive layer between the first electrode and the second electrode, wherein the emissive layer includes the diarylethene derivative compound represented by Formula 1.

According to another aspect of the present invention, there is provided a method of manufacturing an organic EL device, including forming a first electrode, forming an organic layer including the diarylethene derivatives represented by Formula 1 on the first electrode, and forming a second electrode on the organic thin layer.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
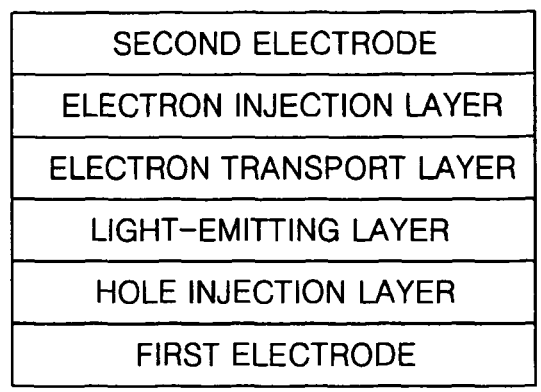
FIG. 1A, 1B and 1C are sectional views of organic electroluminescent (EL) devices according to embodiments of the present invention.

Hereinafter, the present invention will be described in detail by explaining embodiments of the invention with reference to attached drawings.

According to an embodiment of the present invention, there is provided an organic light-emitting compound that is a cis-diarylethene derivative represented by Formula 1:

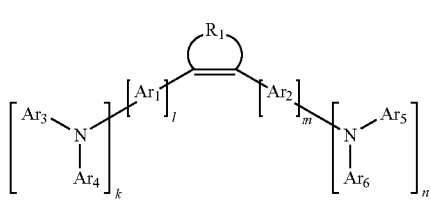

<Formula 1> where $R_1$ is a substituted or unsubstituted $C_1$-$C_{30}$ alkylene group, an alkenylene group, or an alkynylene group;

$Ar_1$ and $Ar_2$ are each independently a substituted or unsubstituted $C_6$-$C_{30}$ arylene group or a substituted or unsubstituted $C_2$-$C_{30}$ heteroarylene group;

$Ar_3$, $Ar_4$, $Ar_5$ and $Ar_6$ are each independently a substituted or unsubstituted $C_6$-$C_{30}$ aryl group, or a substituted or unsubstituted $C_2$-$C_{30}$ heteroaryl group;

$Ar_3$ and $Ar_4$ can be linked to form a ring, and $Ar_5$ and $Ar_6$ can be linked to form a ring;

l and m are each independently integers from 1 to 6; and k and n are each independently integers from 0 to 6, wherein at least one of k and n is larger than or equal to 1.

More particularly, $R_1$ in the compound represented by Formula 1 can be a substituted or unsubstituted methylene group, a substituted or unsubstituted ethylene group, a substituted or unsubstituted propylene group, a substituted or unsubstituted butylene group, a substituted or unsubstituted pentylene group, a substituted or unsubstituted hexylene group, a substituted or unsubstituted heptylene group, a substituted or unsubstituted octylene group, a substituted or unsubstituted nonylene group, or a substituted or unsubstituted decylene group, but is not limited thereto. $R_1$ is preferably a substituted or unsubstituted ethylene group, a substituted or unsubstituted propylene group, and a substituted or unsubstituted butylene group. More preferably, $R_1$ is a substituted or unsubstituted propylene group.

The terms "alkylene group", "alkenylene group", and "alkynylene group" include "cycloalkylene group", "cycloalkenylene group", and "cycloalkynylene group", respectively. That is, $R_1$ can also be a substituted or unsubstituted cycloalkylene group, a substituted or unsubstituted cycloalkenylene group, or a substituted or unsubstituted cycloalkynylene group.

In the compound of Formula 1, $Ar_1$, and $Ar_2$ each independently can be a substituted or unsubstituted benzene, a substituted or unsubstituted naphthalene, a substituted or unsubstituted anthracene, a substituted or unsubstituted phenanthrene, a substituted or unsubstituted fluorene, a substituted or unsubstituted carbazole, a substituted or unsubstituted thiophene, a substituted or unsubstituted thiazole, or a derivative thereof, but are not limited thereto.

In the compound of Formula 1, a substituent group of the substituted alkylene group, the substituted alkenylene group, the substituted alkynylene group, the substituted arylene group, the substituted heteroarylene group, the substituted aryl group, and the substituted heteroaryl group may be at least one selected from the group consisting of —F, —Cl, —Br, —CN, —NO$_2$, —OH; a $C_1$-$C_{20}$ alkyl group which is unsubstituted or substituted with —F, —Cl, —Br, —CN, —NO$_2$ or —OH; a $C_1$-$C_{20}$ alkoxy group which is unsubstituted or substituted with —F, —Cl, —Br, —CN, —NO$_2$ or —OH; a $C_6$-$C_{30}$ aryl group which is unsubstituted or substituted with —F, —Cl, —Br, —CN, —NO$_2$ or —OH; a $C_2$-$C_{30}$ heteroaryl group which is unsubstituted or substituted with —F, —Cl, —Br, —CN, —NO$_2$ or —OH; and a $C_5$-$C_{20}$ cycloalkyl group which is unsubstituted or substituted with —F, —Cl, —Br, —CN, —NO$_2$ or —OH, but is not limited thereto.

More particularly, in the above compounds of Formula 1, $Ar_1$ and $Ar_2$ each independently may be one selected from the group consisting of a phenylene group, a $C_1$-$C_{10}$ alkylphenylene group, a $C_1$-$C_{10}$ alkoxyphenylene group, a halophenylene group, a cyanophenylene group, a dicyanophenylene group, a trifluoromethoxyphenylene group, an o-, m-, or p-tolylene group, an o-, m- or p-cumenylene group, a mesitylene group, a phenoxyphenylene group, an (α,α-dimethylbenzene)phenylene group, a ($C_1$-$C_{10}$ alkylcyclohexyl)phenylene group, an (anthryl)phenylene group, a biphenylene group, a $C_1$-$C_{10}$ alkylbiphenylene group, a $C_1$-$C_{10}$ alkoxybiphenylene group, a pentalenyl group, an indenylene group, a naphthylene group, a $C_1$-$C_{10}$ alkylnaphthylene group, a $C_1$-$C_{10}$ alkoxynaphthylene group, a halonaphthylene group, a cyanonaphthylene group, a biphenylenylene group, a $C_1$-$C_{10}$ alkyl biphenylenylene group, a $C_1$-$C_{10}$ alkoxy biphenylenylene group, a biphenylanthrylene group, an anthrylene group, an azulenylene group, a heptalenylene group, an acenaphthylenylene group, a phenanthrenylene group, a fluorenylene group, an anthraquinolylene group, a methylanthrylene group, a phenanthrylene group, a triphenylenylene group, a pyrenylene group, a chrysenylene group, an ethylchrysenylene group, a picenylene group, a perylenylene group, a chloroperylenylene group, a pentaphenylene group, a pentacenylene group, a tetraphenylene group, a hexaphenylene group, a hexacenylene group, a rubicenylene group, a coronenylene group, a trinaphthylenylene group, a heptaphenylene group, a heptacenylene group, a pyranthrenylene group, an ovalenylene group, a carbazolylene group, a $C_{1-10}$ alkyl carbazolylene group, a thienylene group, an indolylene group, a purinylene group, a benzimidazolylene group, a quinolinylene quinolylene group, a benzothiophenylene group, a parathiazinylene group, a pyrrolylene group, a pyrazolylene group, an imidazolylene group, an imidazolinylene group, an oxazolylene group, a thiazolylene group, a triazolylene group, a tetrazolylene group, an oxadiazolylene group, a pyridylene group, a pyridazinylene group, a pyrimidinylene group, a pyrazinylene group and a thianthrenylene group, a pyrrolidinylene group, a pyrazolidinylene group, an imidazolidinylene group, a piperidylene group, a piperazinylene group and a morpholinylene group, but is not limited thereto.

In the compound of Formula 1, $Ar_3$, $Ar_4$, $Ar_5$ and $Ar_6$ each independently may be a phenyl group, a $C_1$-$C_{10}$ alkylphenyl group, a $C_1$-$C_{10}$ alkoxyphenyl group, a halophenyl group, a cyanophenyl group, a dicyanophenyl group, a trifluoromethoxyphenyl group, an o-, m-, or p-tolyl, an o-, m- or p-cumenyl group, a mesityl group, a phenoxyphenyl group, an (α,α-dimethylbenzene)phenyl group, a (N,N'-dimethyl)aminophenyl group, a (N,N'-diphenyl)aminophenyl group, a (N,N'-bis(methylphenyl))aminophenyl group, a (N,N'-dinaphthyl)aminophenyl group, a ($C_1$-$C_{10}$ alkylcyclohexyl)phenyl group, an (anthraceneyl)phenyl group, a biphenyl group, a $C_1$-$C_{10}$ alkylbiphenyl group, a $C_1$-$C_{10}$ alkoxybiphenyl group, a pentalenyl group, an indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group, a $C_1$-$C_{10}$ alkyl biphenylenyl group, a $C_1$-$C_{10}$ alkoxy biphenylenyl group, an anthr[acene]yl group, an azulenyl group, a heptalenyl group, an acenaphthalenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, a $C_{1-10}$ alkyl carbazolyl group, a thienyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridyl group, a pyridazinyl group, a pyrimidinyl group, a pyrazinyl group and a thianthrenyl group(thianthrenyl), a pyrrolidinyl group, a pyrazolidinyl group, an imidazolidinyl group, a piperidinyl group, a piperazinyl group, a carbazolyl group, a benzoxazolyl group, a phenothiazinyl group, a 5H-dibenzoazepinyl group, a 5H-tribenzoazepinyl group and a morpholinyl group, but are not limited thereto.

More particularly, the above organic light-emitting compounds may be compounds represented by Formulae 2 through 16:

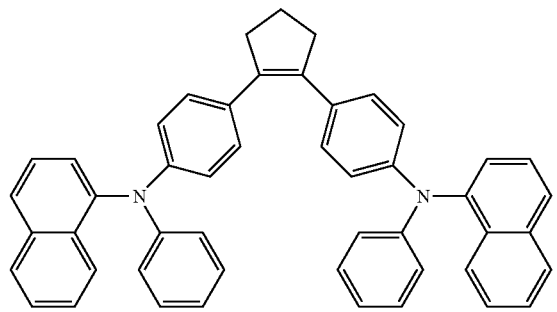

<Formula 2>

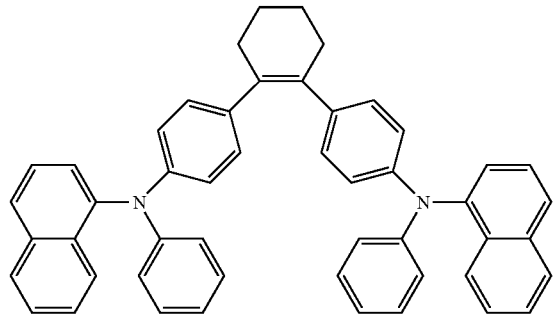

<Formula 3>

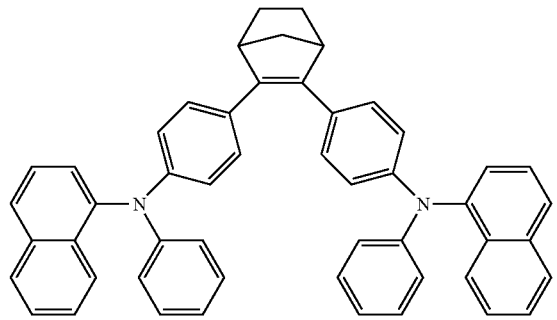

<Formula 4>

<Formula 5>
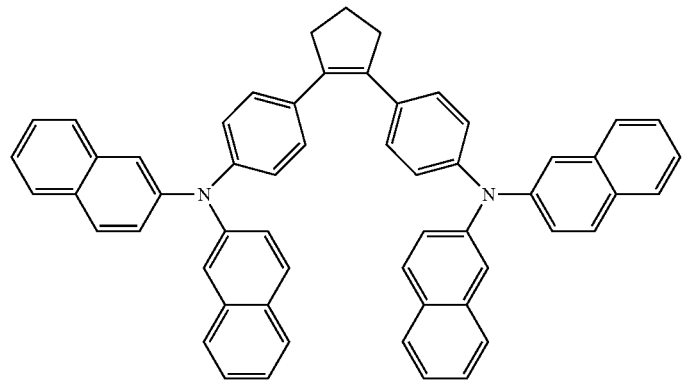
<Formula 6>
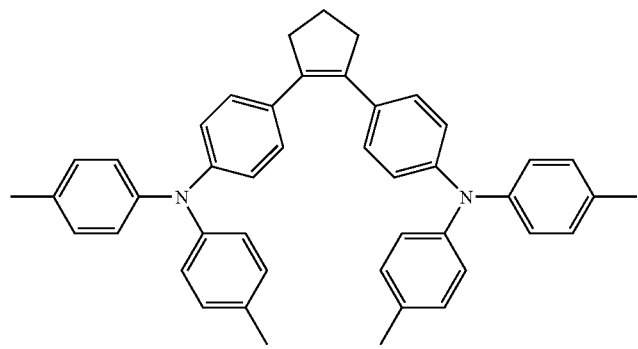
<Formula 7>
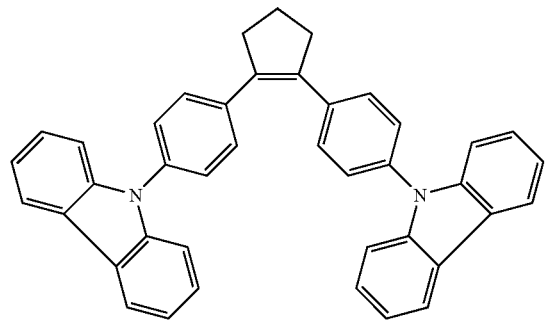
<Formula 8>
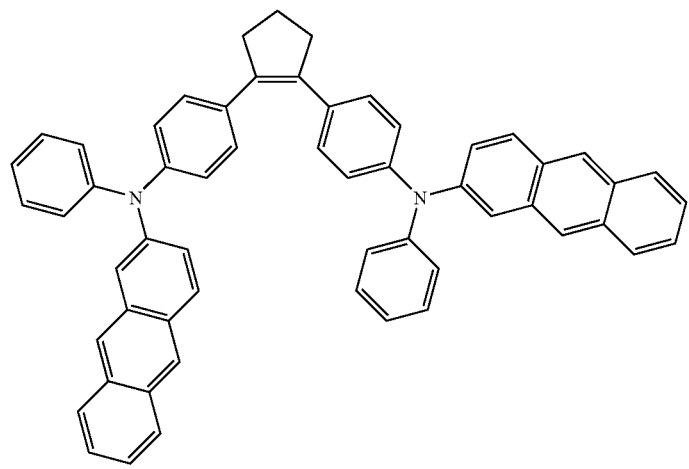

<Formula 9>
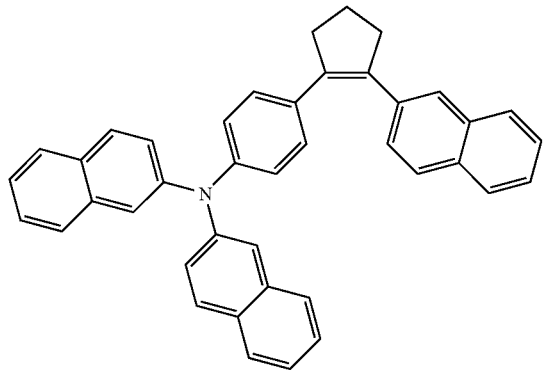
<Formula 10>
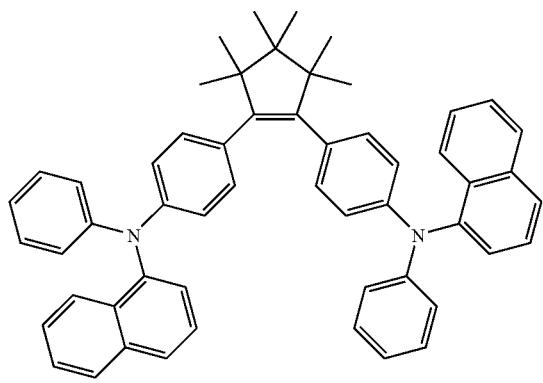
<Formula 11>
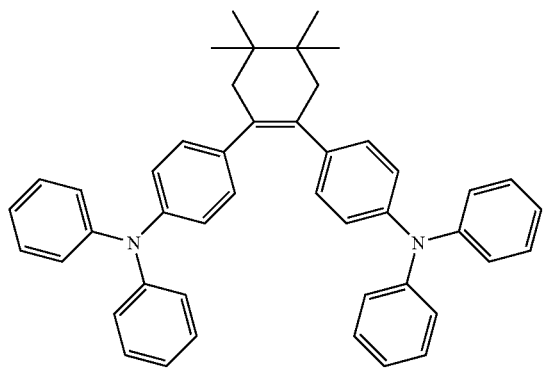
<Formula 12>
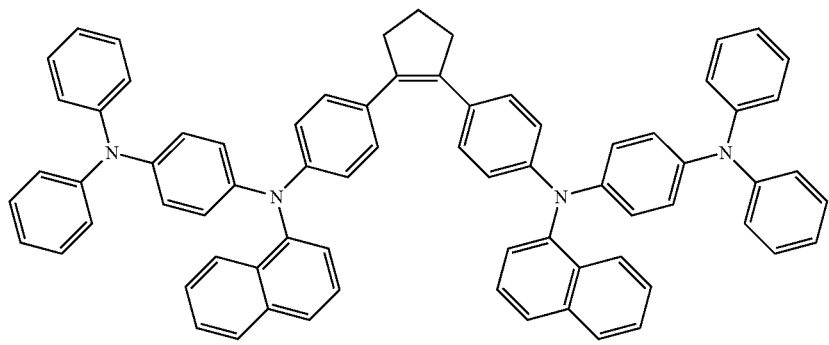

<Formula 13>
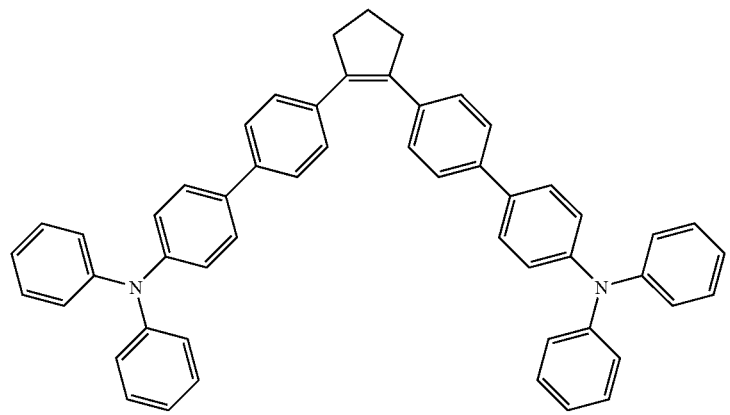
<Formula 14>
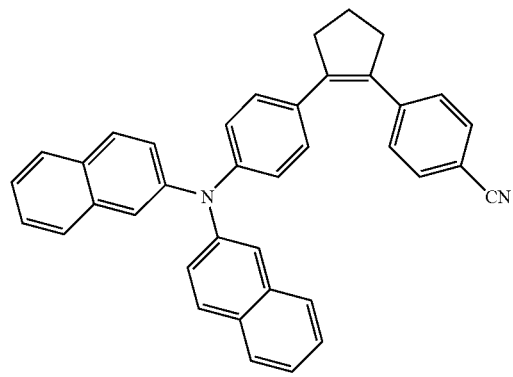
<Formula 15>
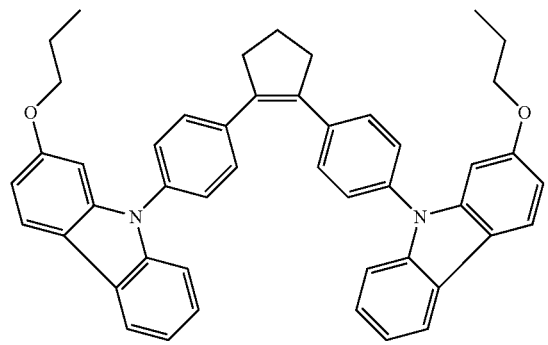
<Formula 16>
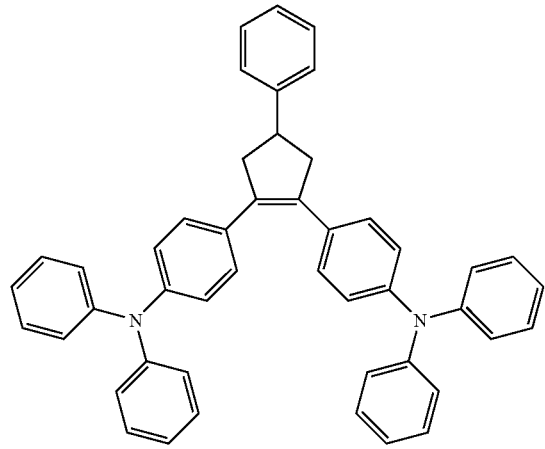

According to another embodiment of the present invention, there is provided an organic electroluminescent (EL) device including a first electrode; a second electrode; and an organic thin layer which is located between the first electrode and the second electrode, wherein the organic thin layer includes the diarylethene derivative represented by Formula 1.

In the organic EL device, the position of the diarylethene group in the organic light-emitting compound is fixed by an aliphatic ring, and thus it is difficult that cis-trans isomerization occurs. Since a trans-diarylethene compound cannot be formed, the crystality of the organic light-emitting compound in a solution state is low, and the solubility thereof is high, and film formability is improved when used in an organic EL device, which is disclosed in Adv. Mater. 2002, 14, 1072, and Chem. Mater. 2005, 17, 1287. The organic EL device according to the embodiments of the present invention provides excellent device characteristics due to the use of the organic light-emitting compound having the above-described structure, which will be described in more detail in the following examples.

An organic EL device according to an embodiment of the present invention may have various structures. An organic EL device according to an embodiment of the present invention can include a first electrode, a second electrode and an organic thin layer which is located between the first electrode and the second electrode. The organic thin layer between the first electrode and the second electrode can include at least one layer selected from the group consisting of a hole injection layer, a hole transport layer, an electron blocking layer, a hole blocking layer, an electron transport layer, and an electron injection layer.

Figure 1B:
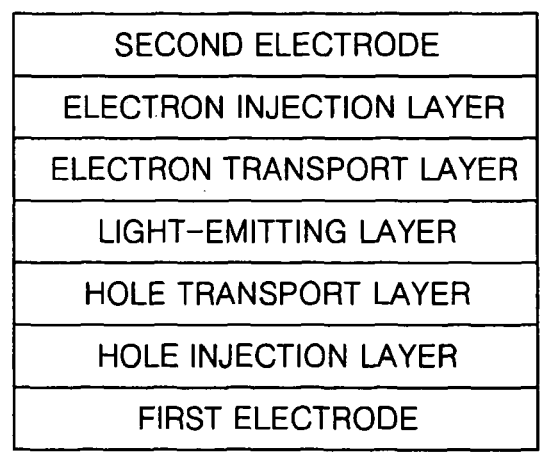
Figure 1C:
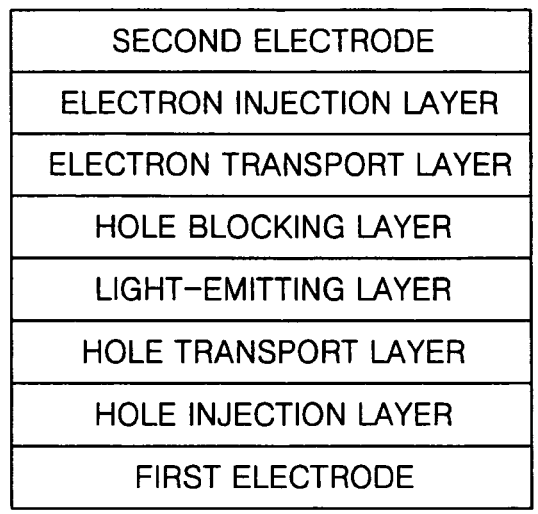

FIG. 1A, 1B and 1C are sectional views of organic EL devices according to embodiments of the present invention. The organic EL device illustrated in FIG. 1A has a first electrode/hole injection layer/emissive layer (also referred to as "light-emitting layer")/electron transport layer/electron injection layer/second electrode structure. The organic EL device illustrated in FIG. 1B has a first electrode/hole injection layer/hole transport layer/emissive layer/electron transport layer/electron injection layer/second electrode structure. The organic EL device illustrated in FIG. 1C has a first electrode/hole injection layer/hole transport layer/emissive layer/hole blocking layer/electron transport layer/electron injection layer/second electrode structure. The emissive layer of the organic EL devices illustrated in FIGS. 1A, 1B and 1C can be formed using the compounds according to the embodiments of the present invention.

The emissive layer of the organic EL devices illustrated in FIGS. 1A, 1B and 1C can include phosphorescent or fluorescent dopants of red, green, blue or white, where the phosphorescent dopants can be an organic metal compound including at least one element selected from the group consisting of Ir, Pt, Os, Ti, Zr, Hf, Eu, Tb and Tm.

Hereinafter, a method of manufacturing an organic EL device according to an embodiment of the present invention is described with reference to the organic EL device illustrated in FIG. 1C.

First, the first electrode, which can be used as an anode, is formed on a substrate by depositing or sputtering a first electrode forming material. The substrate can be any substrate used in common organic light-emitting devices, and may be a glass substrate or a transparent plastic substrate which is excellent in terms of mechanical strength, thermostability, transparency, surface smoothness, ease of treatment and waterproofness. The first electrode can be formed of a material such as ITO, IZO, $SnO_2$, ZnO, or the like which is transparent and highly conductive.

Then the hole injection layer (HIL) can be formed on the first electrode using vacuum deposition, spin coating, casting, Langmuir Blodgett (LB), or the like.

When vacuum deposition is used to form the HIL, deposition conditions may vary according to the compound used to form the HIL, and the structure and thermal properties of the HIL to be formed. In general, however, conditions for vacuum deposition may include a temperature range of 50° C. to 500° C., a pressure range of $10^{-8}$ torr to $10^{-3}$ torr, a deposition speed of 0.01 to 100 Å/sec, and a layer thickness of 10 Å to 5 µm.

When spin coating is used to form the HIL, coating conditions may vary according to the compound used to form the HIL, and the structure and thermal properties of the HIL to be formed. In general, however, conditions for spin coating may include a coating speed of about 2,000 through 5,000 rpm, and a heat treatment temperature of about 80 through 200° C. to remove the solvent after coating.

A material for the HIL is not limited. Examples of the material for the HIL include a phthalocyanine compound, such as copperphthalocyanine, which is disclosed in U.S. Pat. No. 4,356,429, star-burst type amine derivatives, such as TCTA, m-MTDATA, and m-MTDAPB, which are disclosed in Advanced Material, 6, p. 677 (1994), conductive soluble polymers, such as Pani/DBSA (polyaniline/dodecylbenzenesulfonic acid) or PEDOT/PSS (poly(3,4-ethylenedioxythiophene)/poly(4-styrenesulfonate), Pani/CSA (polyaniline/camphor sulfonic acid), or PANI/PSS (polyaniline/poly(4-styrenesulfonate)).

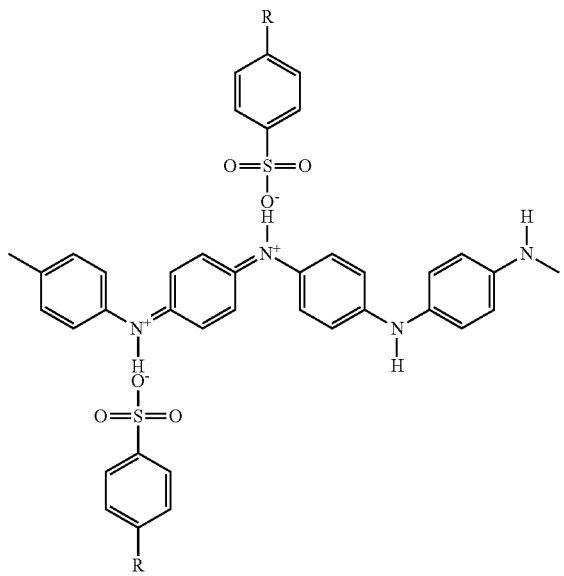

Pani/DBSA

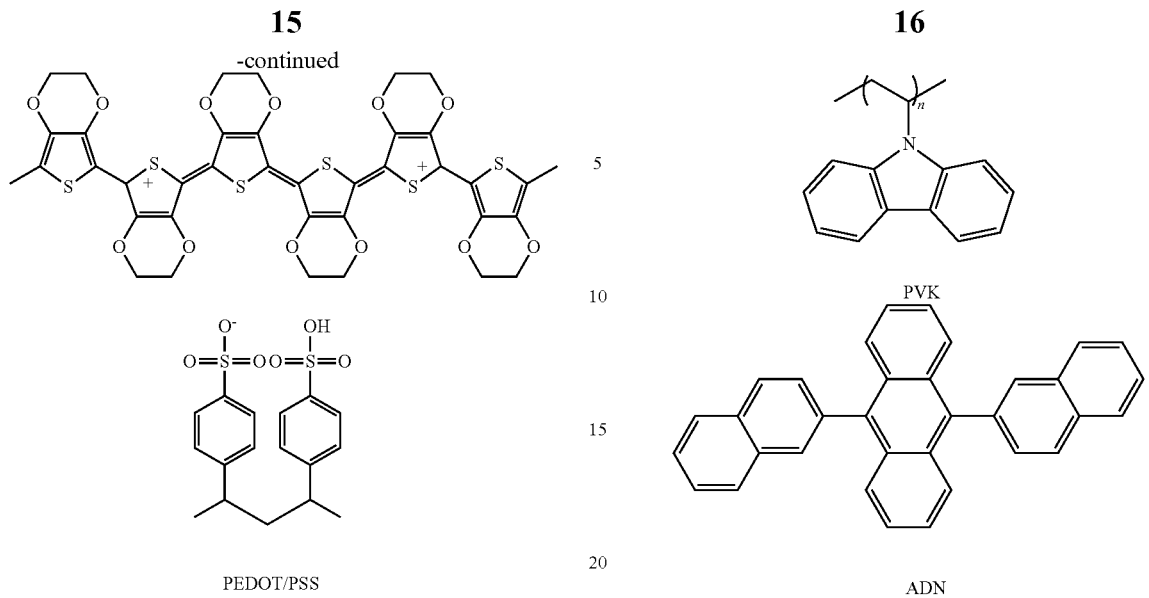

PEDOT/PSS

PVK

ADN

The thickness of the HIL may be about 100 through 10,000 Å, for example, 100 through 1,000 Å. When the thickness of the hole injection layer is less than 100 Å, the hole injection properties can deteriorate. When the thickness of the hole injection layer is greater than 10,000 Å, the turn-on voltage can increase.

Then the hole transport layer (HTL) can be formed on the HTL using vacuum deposition, spin coating, casting, Langmuir Blodgett (LB), or the like. When vacuum deposition or spin coating is used to form the HTL, deposition or coating conditions may vary according to the compounds used to form the HTL. In general, however, the same deposition or coating conditions as used to form the HIL are used.

A material for the HTL is not limited. The HTL can be formed of known hole transport materials, for example, carbazole derivatives such as N-phenylcarbazole, and polyvinylcarbazole, or typical amine derivatives with aromatic fused rings such as N,N'-bis(3-methylphenyl)-N,N'-diphenyl-[1,1-biphenyl]-4,4'-diamine (TPD) and N,N'-di(naphthalene-1-yl)-N,N'-diphenyl benzidine (α-NPD).

The thickness of the HTL may be about 50 through 1,000 Å, for example 100 through 600 Å. When the thickness of the HTL is less than 50 Å, hole transport properties can deteriorate. When the thickness of the HTL is greater than 1,000 Å, the turn-on voltage can increase.

Next, the emissive layer (EML) can be formed on the HTL using vacuum deposition, spin coating, casting, Langmuir Blodgett (LB), or the like. When vacuum deposition or spin coating is used to form the EML, the deposition or coating conditions may vary according to the compound used to form the EML. In general, however, the same deposition or coating conditions as used to form the HIL are used to form the EML.

The emissive layer may be formed using the organic light-emitting compound represented by Formula 1 according to an embodiment of the present invention as described above. The compound of Formula 1 can be used together with organic semiconductors, such as pentacene, polythiophene, tetrathiafulvalene, etc.

The organic light-emitting compound of Formula 1 can also be used together with a suitable known host material. Examples of the host material include, for example, Alq3, CBP (4,4'-N,N'-dicabazole-biphenyl), PVK (poly(n-vinyl-cabazole)), ADN (9,10-di-(2-naphthyl) anthracene), etc.

The emissive layer can also be formed using various fluorescent or phosphorescent dopants, in addition to the compounds according to embodiments of the present invention. The fluorescent dopants can be DPAVBi, IDE102 or IDE105, which is available from Idemitsu Corporation, or C545T, which is available from Hayashibara Corporation. The phosphorescent dopants can be PtOEP and RD 61 of UDC Corporation as red dopants, Ir(PPy)3(PPy=2-phenylpyridine) as green dopants, or F2Irpic as blue dopants.

The doping concentration is not limited, but usually ranges from 0.01 to 15 parts by weight based on 100 parts by weight of the host.

The thickness of the EML may be about 100 through 1,000 Å, for example 200 through 600 Å. When the thickness of the EML is less than 100 Å, emissive properties can deteriorate. When the thickness of the EML is greater than 1,000 Å, turn-on voltage can increase.

When phosphorescent dopants are used in the emissive layer, a hole blocking layer (HBL) can be formed on the hole transport layer (HTL) using vacuum deposition, spin coating, casting, Langmuir Blodgett (LB), or the like to prevent triplet excitons or holes from diffusing into an electron transport layer (ETL). When vacuum deposition or spin coating is used to form the HBL, deposition or coating conditions may vary according to the compounds used to form the HBL. In general, however, the same deposition or coating conditions as used to form the HIL are used. Known hole blocking materials such as oxadiazole derivatives, triazole derivatives, phenanthroline derivatives, BCP, etc. can be used to form the HBL.

The thickness of the HBL may be about 50 through 1,000 Å, for example 100 through 300 Å. When the thickness of the HBL is less than 50 Å, hole-blocking properties can deteriorate. When the thickness of the HBL is greater than 1,000 Å, turn-on voltage can increase.

Next, the electron transport layer (ETL) can be formed on the HBL using vacuum deposition, spin coating, casting, or the like. When vacuum deposition or spin coating is used to form the ETL, the deposition or coating conditions may vary according to the compounds used to form the ETL. In general, however, the same deposition or coating conditions as used to form the HIL are used to form the ETL. Known electron transport materials such as quinoline derivatives, in particular, tris(8-quinolinorate)aluminium (Alq3) and TAZ can be used to form the ETL.

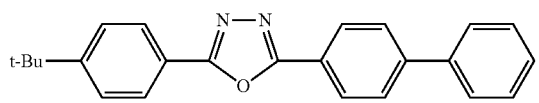

TAZ

The thickness of the ETL may be about 100 through 1,000 Å, for example, 200 through 500 Å. When the thickness of the ETL is less than 100 Å, electron-transporting properties may deteriorate. When the thickness of the ETL is greater than 1,000 Å, turn-on voltage can increase.

Then the electron injection layer (EIL), which makes the injection of electrons from the cathode easier, can be formed on the ETL. Known electron injection layer forming materials such as LiF, NaCl, CsF, $Li_2O$, and BaO can be used to form the EIL, but the present invention is not limited thereto. The deposition or coating conditions used to form the EIL can vary according to the compounds used to form the EIL. In general, however, the same deposition or coating conditions as used to form the HIL are used to form the EIL.

The thickness of the EIL may be about 1 through 100 Å, for example, 5 through 50 Å. When the thickness of the EIL is less than 1 Å, electron-injection properties may deteriorate. When the thickness of the EIL is greater than 100 Å, turn-on voltage can increase.

Finally, the second electrode, which can be used as a cathode, can be formed on the ETL using vacuum deposition, sputtering, or the like. The second electrode can be formed of metals having a low work function, alloys, electrically conductive compounds, or compounds thereof. For example, Li, Mg, Al, Al—Li, Ca, Mg—In, Mg—Ag can be used to form the second electrode. Alternatively, a transparent cathode formed of ITO or IZO can be employed to manufacture a top-emission type organic EL device.

The organic EL device according to the embodiments of the present invention may have the structure of FIG. 1C, which includes the first electrode/HIL/HTL/EML/HBL/ETL/EIL/second electrode, and various structures, which will be described in more detail in the following examples. Some of the layers can be omitted if required.

According to another embodiment of the present invention, there is provided a method of manufacturing an organic EL device, including forming a first electrode; forming an organic thin layer including the diarylethene derivative represented by Formula 1 on the first electrode; and forming a second electrode on the organic thin layer.

The organic thin layer of the organic EL device may be formed using a wet process such as spin coating, inkjet printing or spray printing, or using heat transfer, but the present invention is not limited thereto.

The organic light-emitting compound of Formula 1 can be synthesized using a commonly used synthesis method. Structures of all compounds synthesized in the following examples were identified using 1H NMR and a mass spectrometer.

Hereinafter, the present invention will be described more specifically with reference to the following examples. However, these examples are provided for illustrative purposes only and are not intended to limit the scope of the invention.

Synthesis Examples of Compounds 2 through 5, which are respectively represented by Formulae 2 through 5, and Examples are provided in detail below. However, these examples are provided for illustrative purposes only and are not intended to limit the scope of the invention.

SYNTHESIS EXAMPLE

Synthesis Example 1

Synthesis of Intermediate A

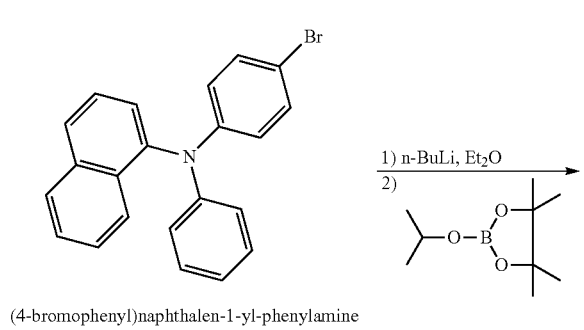

(4-bromophenyl)naphthalen-1-yl-phenylamine

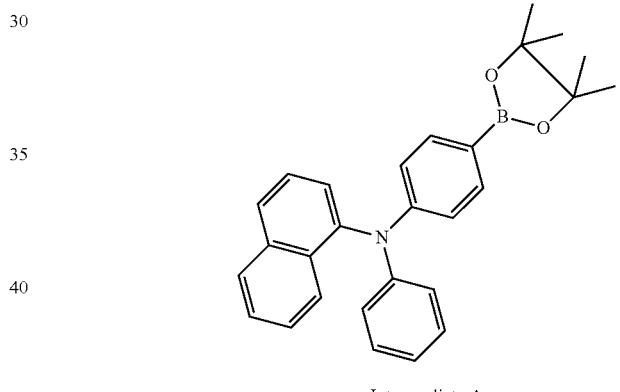

Intermediate A 3.7 g (10 mmol) of (4-bromophenyl)naphthalen-1-yl-phenylamine was dissolved in 100 ml of THF and cooled to −78° C. 4.8 ml (12 mmol) of 2.5M n-butyllithium was added slowly to the THF solution and maintained at the same temperature as above for an hour to allow reaction. 2.2 g (12 mmol) of 2-isopropoxy-4,4,5,5-tetramethyl-1,3,2-dioxaborolane was added to the reactant solution, maintained at the same temperature as above for an hour to allow reaction, heated to room temperature (RT) and stirred for 24 hours. Water was added to end the reaction, and 300 ml of chloroform was added. The resulting organic layer was washed with 200 ml of water and dried with anhydride magnesium sulfate. 3.4 g of Naphthalen-1-yl-phenyl[4-(4,4,5,5-tetramethyl[1,3,2]dioxaborolan-2-yl)phenylamine (intermediate A) was obtained through silica chromatography with a yield of 81%.

$^1$H-NMR ($CDCl_3$, 300 MHz): 7.8 (d, 2H), 7.7 (d, 1H), 7.6 (d, 2H), 7.4 (m, 2H), 7.3 (m,2H), 7.2 (d, 2H), 7.1 (d, 2H), 6.9 (m, 3H), 1.3 (s,12H)

Synthesis Example 2

Synthesis of Intermediate B

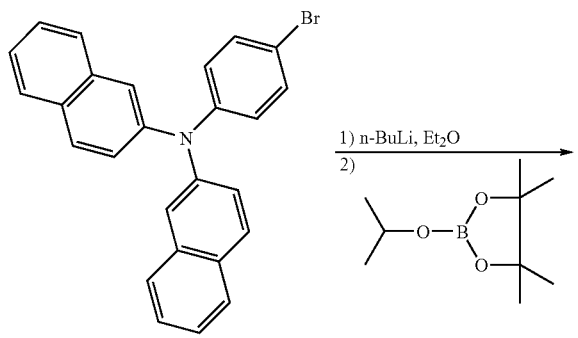

(4-bromophenyl)dinaphthalene-2-ylamine

Intermediate B 8.5 g (20 mmol) of (4-bromophenyl)dinaphthalene-2-ylamine was dissolved in 100 ml of THF and was cooled to −78° C. 9.6 ml (24 mmol) of 2.5M n-butyllithium was added slowly to the THF solution and maintained at the same temperature as above for an hour to allow reaction. 4.4 g (24 mmol) of 2-isopropoxy-4,4,5,5-tetramethyl-1,3,2-dioxaborolane was added to the reaction solution, and was maintained at the same temperature as above for an hour. The reaction solution was heated to room temperature (RT) and stirred for 24 hours. Water was added to end the reaction. 300 ml of chloroform was added to the solution and washed with 200 ml of water. The resulting organic layer was dried with anhydride magnesium sulfate. 7.3 g of dinaphthalen-2-yl-[4-(4,4,5,5-tetramethyl[1,3,2]dioxaborolane-2-yl)phenyl]amine (intermediate B) was obtained through silica chromatography with a yield of 77%.

$^1$H-NMR (CDCl$_3$, 300 MHz): 7.7 (m, 6H), 7.6 (m, 2H), 7.5 (d, 2H), 7.4 (m, 4H), 7.3 (dd, 2H), 7.1 (d, 2H), 1.3 (s,12H)

EXAMPLE

Example 1

Synthesis of Compound 2 of Formula 2

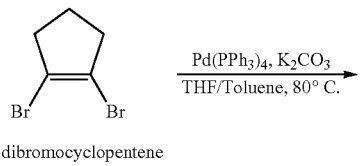

Intermediate A

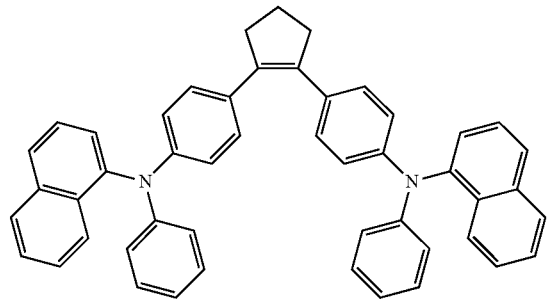

1,2-dibromocyclopentene

Compound 2

0.15 g (0.7 mmol) of 1,2-dibromocyclopentene was dissolved in 30 ml of THF. 0.58 g(1.4 mmol) of intermediate A, 160 mg (0.14 mmol) of tetrakis(triphenylphosphine) palladium (Pd(PPh3)), and 960 mg (7 mmol) of potassium carbonate (K$_2$CO$_3$) were dissolved in 30 ml of toluene and 5 ml of water. The solution was added to the above THF solution and refluxed for 24 hours. After the reaction ended, the solvent was removed by evaporation. 100 ml of ethyl acetate was added thereto and washed with 100 ml of water. An organic layer was collected and dried with anhydride magnesium sulfate. 0.16 g of Compound 2 of Formula 2 was obtained through silica chromatography with a yield of 35%.

$^1$H-NMR (CDCl$_3$, 300 MHz): 7.8 (m, 6H), 7.4 (m, 14H), 6.9 (m, 8H), 6.6 (m, 4H), 2.7 (t, 4H), 1.9 (m, 2H).

Example 2

Synthesis of Compound 3 of Formula 3

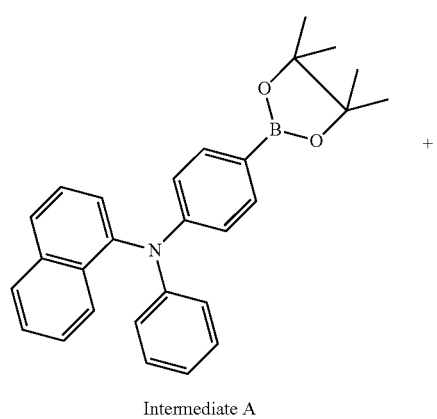

Intermediate A

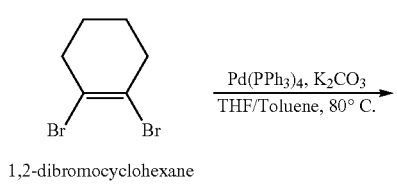

1,2-dibromocyclohexane

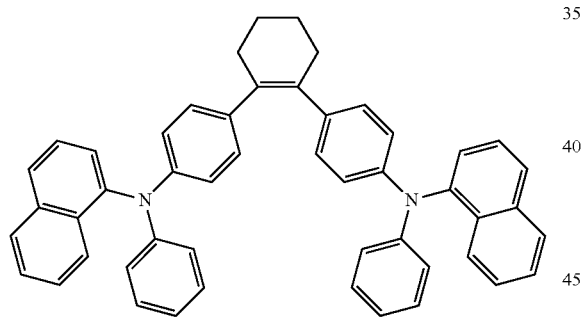

Compound 3

0.23 g (1 mmol) of 1,2-dibromocyclohexane was dissolved in 30 ml of THF. Then, 0.82 g (2 mmol) of intermediate A, 57 mg (0.05 mmol) of tetrakis(triphenylphosphine)palladium (Pd(PPh3)), and 690 mg (5 mmol) of potassium carbonate were dissolved in 30 ml of toluene and 5 ml of water, which was added to the above THF solution and stirred for 24 hours. After the reaction ended, the solvent was evaporated. 100 ml of ethyl acetate was added, and the resulting layer was washed with 100 ml of water. The obtained organic layer was dried with anhydride magnesium sulfate. 0.27 g of Compound 3 of Formula 3 was obtained through silica chromatography with a yield of 40%.

$^1$H-NMR (CDCl$_3$, 300 MHz): 7.8 (m, 6H), 7.4 (m, 14H), 6.9 (m, 8H), 6.6 (m, 4H), 2.7 (t, 4H), 1.6 (m, 4H)

Example 3

Synthesis of Compound 4 of Formula 4

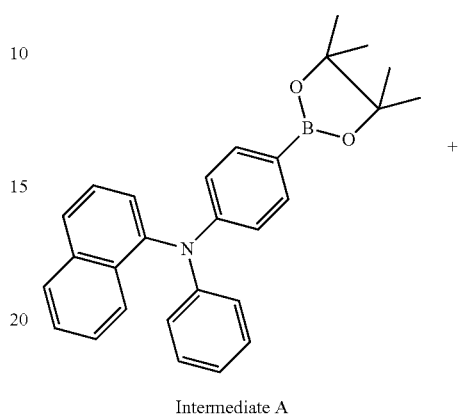

Intermediate A

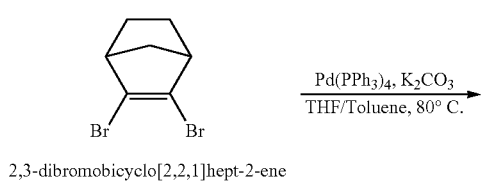

2,3-dibromobicyclo[2,2,1]hept-2-ene

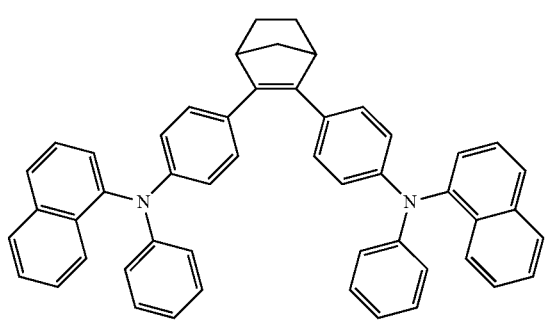

Compound 4

0.28 g (1.1 mmol) of 2,3-dibromobicyclo[2,2,1]hept-2-ene (1.1 mmol) was dissolved in 30 ml of THF. Then 0.90 g (2.2 mmol) of intermediate A, 63 mg (0.055 mmol) of tetrakis (triphenylphosphine)palladium (Pd(PPh3)), and 760 mg (11 mmol) of potassium carbonate were dissolved in 30 ml of toluene and 5 ml of water, added to the above THF solution, and refluxed for 24 hours. After the reaction ended, the solvent was removed by evaporation. Then, 100 ml of ethyl acetate was added thereto and washed with 100 ml of water. An organic layer was collected and dried with anhydride magnesium sulfate. 0.33 g of Compound 4 of Formula 4 was obtained through silica chromatography with a yield of 44%.

$^1$H-NMR (CDCl$_3$, 300 MHz): 7.8 (m, 6H), 7.4 (m, 14H), 6.8 (m, 8H), 6.7 (m, 4H), 2.9 (t, 2H), 1.6 (m, 6H)

Example 4

Synthesis of Compound 5 of Formula 5

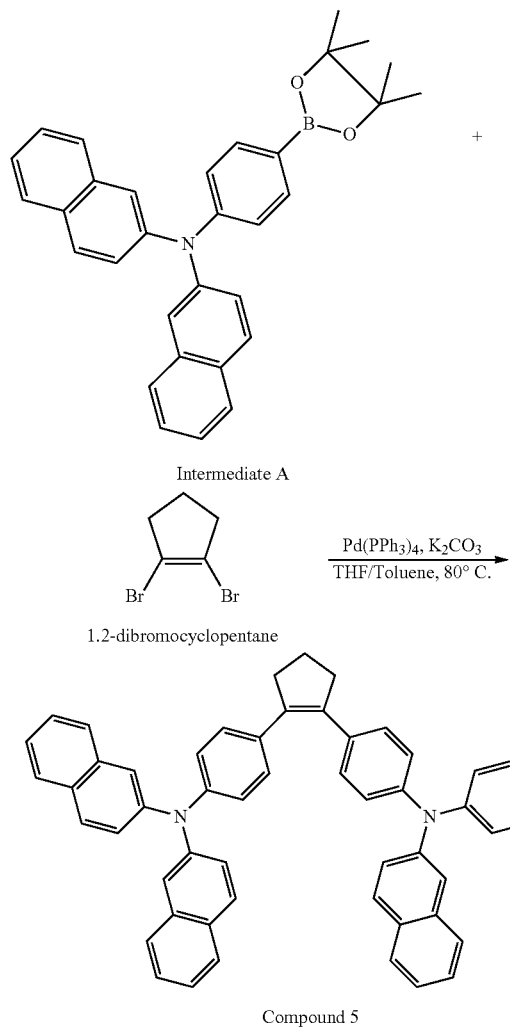

0.42 g (1.0 mmol) of 1,2-dibromocyclopentene was dissolved in 30 ml of THF. 0.82 g (2 mmol) of intermediate B, 57 mg (0.05 mmol) of tetrakis(triphenylphosphine)palladium (Pd(PPh3), and 690 mg (5 mmol) of potassium carbonate were dissolved in 30 ml of toluene and 5 ml of water, and the solution was added to the above THF solution and refluxed for 24 hours. After the reaction ended, the solvent was removed by evaporation. 100 ml of ethyl acetate was added thereto and washed with 100 ml of water. An organic layer was collected and dried with anhydride magnesium sulfate. 0.26 g of Compound 5 of Formula 5 was obtained through silica chromatography with a yield of 35%.

$^1$H-NMR (CDCl$_3$, 300 MHz): 7.7 (m, 8H), 7.5 (m, 8H), 7.4 (m, 16H), 7.1 (m, 4H), 2.9 (t, 4H), 1.9 (m, 2H)

Comparative Example 1

An organic electroluminescent (EL) device was manufactured in the same manner as used in Example 1 except that Compound 17 of Formula 17 was used as a host instead of Compound 2. The organic EL device will be referred to as Sample 6.

<Formula 17>

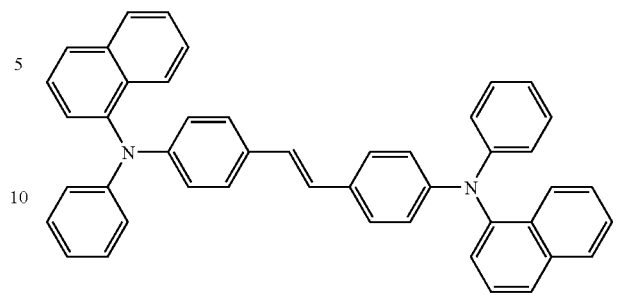

Evaluation 1: Evaluation of Light-Emitting Property of Compounds 2 through 5

The light-emitting properties of Compounds 2 through 5 were evaluated by measuring UV absorption spectra and photoluminescence (PL) spectra.

First, Compounds 2 through 5 were diluted in toluene to a concentration of 0.2 mM and a UV absorption spectrum was measured using a Shimadzu UV-350 Spectrometer. Then Compounds 2 through 5 were diluted in toluene to a concentration of 10 mM, and a PL spectrum was measured using an ISC PC1 Spectrofluorometer with a Xenon Lamp. The results are shown in Table 1, and the spectrum of Compound 2 is illustrated in FIG. 2.

TABLE 1

| Compound No. | Maximum Absorption Wavelength (nm) | Maximum PL Wavelength (nm) |
| --- | --- | --- |
| Compound 2 | 330 | 450 |
| Compound 3 | 328 | 450 |
| Compound 4 | 330 | 452 |
| Compound 5 | 370 | 456 |

Figure 2:
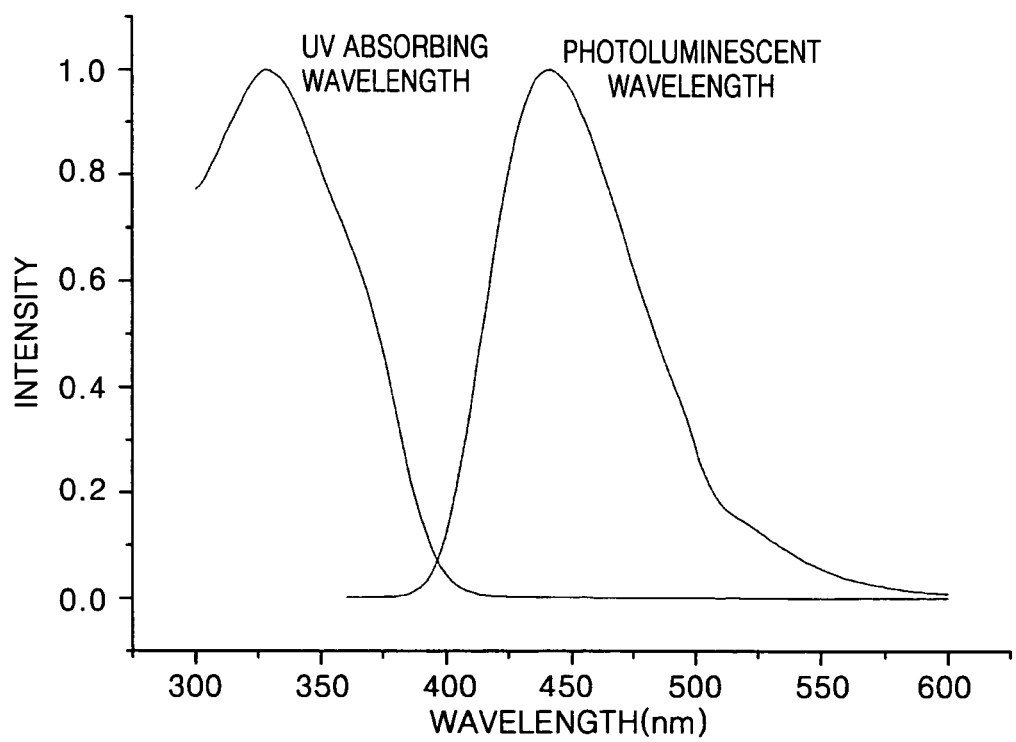
FIG. 2 is a graph showing the intensity of UV light and photoluminescence (PL) of Compound 2 according to an embodiment of the present invention.

Referring to Table 1 and FIG. 2, Compounds 2 through 5 according to the embodiments of the present invention have light-emitting properties which are suitable for organic EL devices.

Evaluation 2: Evaluation of Properties of Samples

An organic EL device was manufactured using Compound 2 as a dopant for an emissive layer according to the following process:

ITO/PEDOT(50 nm)/compound 2(50 nm)/Alq3(20 nm)/LiF(1 nm)/Al(200 nm).

An anode was prepared by cutting an ITO glass substrate having a 15 Ω/cm$_2$ (1200 Å) (available from Corning Corporation) to a size of 50 mm×50 mm×0.7 mm, and performing microwave-washing in isopropyl alcohol and pure water respectively for 5 minutes, and UV ozone-washing for 30 minutes. PEDOT-PSS (Al4083) (available from Bayer Corporation) was coated on the above substrate and was then heat-treated at 120° C. for 5 hours to form a 500 Å hole injection layer (HIL). The toluene solution of Compound 2 (10 parts by weight of Compound 2 based on 100 parts by weight of toluene) was spin-coated on the HIL and heat-treated at 80° C. for 30 minutes to form an emissive layer (EML) having a thickness of 50 nm. Then Alq$_3$ compound was vacuum-deposited on the EML to a thickness of 20 nm to form an electron transport layer (ETL). On the ETL, 10 Å of LiF (an electron injection layer) and 2000 Å of Al (cathode) were sequentially vacuum-deposited to complete the manufacture of an organic EL device as illustrated in FIG. 1A. This organic EL device will be referred to as Sample 2.

Organic EL devices were manufactured using Compounds 3 through 6 in the same manner as used in Evaluation 2. These organic EL devices will be referred to as Samples 3 through 6, respectively.

Figure 3:
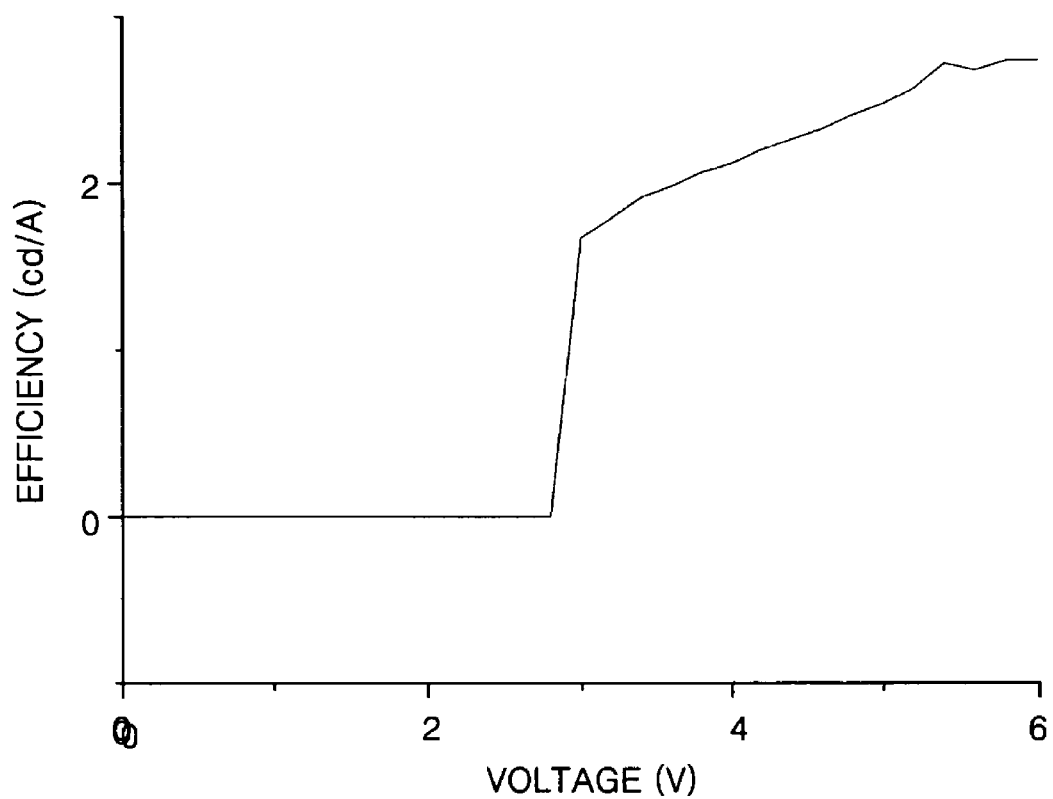
FIG. 3 is a graph showing the electrical efficiency of Sample 2, that is, an organic EL device employing compounds according to an embodiment of the present invention.

Turn-on voltage, luminance, and efficiency of Samples 2 through 6 were measured using a PR650 (Spectroscan) Source Measurement Unit, and the results are shown in Table 2 and a graph showing the electrical efficiency of Sample 2 is shown in FIG. 3.

TABLE 2

| Sample No | Turn-on voltage (V) | Luminance (cd/m2) | Efficiency (cd/A) |
|---|---|---|---|
| Sample 2 | 3 | 2785 | 2.75 |
| Sample 3 | 3 | 2662 | 2.60 |
| Sample 4 | 3 | 2710 | 2.65 |
| Sample 5 | 3 | 2837 | 2.80 |
| Sample 6 | 3 | 2003 | 1.98 |

Referring to Table 2 and FIG. 3, the organic EL device using cis-diarylethene derivatives as an organic light-emitting compound according to an embodiment of the present invention has superior luminance and emission efficiency compared to when using Compound 17.

Since the organic light-emitting compound according to the present invention contains a cis-diarylethene group which is linked with an aliphatic ring, crystallization of the organic light-emitting compound is unlikely to occur, and the compound is highly soluble in organic solvents and easily provides liquid formulation with organic solvents. Thus, it is easy to use the compound in organic EL devices. An organic EL device manufactured using the compound can have a thermostable organic layer and have excellent features in terms of turn-on voltage, efficiency, and color purity.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An organic electroluminescent (EL) device comprising:
a first electrode;
a second electrode; and
an organic layer comprising an emissive layer between the first electrode and the second electrode, the emissive layer comprising an organic light-emitting compound of a cis-diarylethene derivative represented by Formula 1:

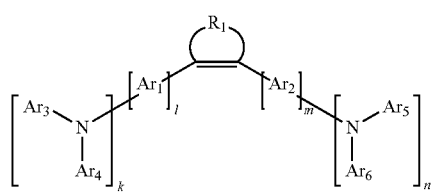

(1)

where $R_1$ is a substituted or unsubstituted $C_1$-$C_{30}$ alkylene group, an alkenylene group, or an alkynylene group;
$Ar_1$ and $Ar_2$ are each independently a substituted or unsubstituted $C_6$-$C_{30}$ arylene group, or a substituted or unsubstituted $C_2$-$C_{30}$ heteroarylene group;
$Ar_3$, $Ar_4$, $Ar_5$ and $Ar_6$ are each independently a substituted or unsubstituted $C_6$-$C_{30}$ aryl group, or a substituted or unsubstituted $C_2$-$C_{30}$ heteroaryl group;
$Ar_3$ and $Ar_4$ can be linked to form a ring, and $Ar_5$ and $Ar_6$ can be linked to form a ring;
l and m are each independently integers form 1 to 6; and
k and n are each independently integers from 0 to 6, wherein at least one of k and n is larger than or equal to 1.

2. The organic electroluminescent device of claim 1, wherein $R_1$ is a substituted or unsubstituted methylene group, a substituted or unsubstituted ethylene group, a substituted or unsubstituted propylene group, a substituted or unsubstituted butylene group, a substituted or unsubstituted pentylene group, a substituted or unsubstituted hexylene group, a substituted or unsubstituted heptylene group, a substituted or unsubstituted octylene group, a substituted or unsubstituted nonylene group, or a substituted or unsubstituted decylene group.

3. The organic electroluminescent device of claim 1, wherein $R_1$ is a substituted or unsubstituted cycloalkylene group, a substituted or unsubstituted cycloalkenylene group, or a substituted or unsubstituted cycloalkynylene group.

4. The organic electroluminescent device of claim 1, wherein $Ar_1$, and $Ar_2$ are each independently a substituted or unsubstituted benzene, a substituted or unsubstituted naphthalene, a substituted or unsubstituted anthracene, a substituted or unsubstituted phenanthrene, a substituted or unsubstituted fluorene, a substituted or unsubstituted carbazole, a substituted or unsubstituted thiophene, a substituted or unsubstituted thiazole, or a derivative thereof.

5. The organic electroluminescent device of claim 1, wherein the substituent groups of the substituted alkylene group, the substituted alkenylene group, the substituted alkynylene group, the substituted arylene group, the substituted heteroarylene group, the substituted aryl group, and the substituted heteroaryl group are at least one selected from the group consisting of —F, —Cl, —Br, —CN, —NO$_2$, —OH; a $C_1$-$C_{20}$ alkyl group which is unsubstituted or substituted with —F, —Cl, —Br, —CN, —NO$_2$ or —OH, a $C_1$-$C_{20}$ alkoxy group which is unsubstituted or substituted with —F, —Cl, —Br, —CN, —NO$_2$ or —OH; a $C_6$-$C_{30}$ aryl group which is unsubstituted or substituted with —F, —Cl, —Br, —CN, —NO$_2$ or —OH; a $C_2$-$C_{30}$ heteroaryl group which is unsubstituted or substituted with —F, —Cl, —Br, —CN, —NO$_2$ or —OH; and a $C_5$-$C_{20}$ cycloalkyl group which is unsubstituted or substituted with —F, —Cl, —Br, —CN, —NO$_2$ or —OH.

6. The organic electroluminescent device of claim 1, wherein $Ar_1$ or $Ar_2$ is each independently selected from the group consisting of a phenylene group, a $C_1$-$C_{10}$ alkylphenylene group, a $C_1$-$C_{10}$ alkoxyphenylene group, a halophenylene group, a cyanophenylene group, a dicyanophenylene group, a trifluoromethoxyphenylene group, an o-, m-, or p-tolylene group, an o-, m- or p-cumenylene group, a mesitylene group, a phenoxyphenylene group, an (α,α-dimethylbenzene)phenylene group, a ($C_1$-$C_{10}$ alkylcyclohexyl)phenylene group, an (anthryl)phenylene group, a biphenylene group, a $C_1$-$C_{10}$ alkylbiphenylene group, a $C_1$-$C_{10}$ alkoxybiphenylene group, a pentalenyl group, an indenylene group, a naphthylene group, a $C_1$-$C_{10}$ alkylnaphthylene group, a $C_1$-$C_{10}$ alkoxynaphthylene group, a halonaphthylene group, a cyanonaphthylene group, a biphenylenylene group, a $C_1$-$C_{10}$ alkyl biphenylenylene group, a $C_1$-$C_{10}$alkoxy biphenylenylene group, a biphenylanthrylene group, an anthrylene group, an azulenylene group, a heptalenylene group, an acenaphthylenylene group, a phenanthrenylene group, a fluorenylene group, an anthraquinolylene group, a methylanthrylene group, a phenanthrylene group, a triphenylenylene group, a pyrenylene group, a chrysenylene group, an ethyl-chrysenylene group, a picenylene group, a perylenylene group, a chloroperylenylene group, a pentaphenylene group, a pentacenylene group, a tetraphenylenylene group, a hexaphenylene group, a hexacenylene group, a rubicenylene group, a coronenylene group, a trinaphtylenylene group, a heptaphenylene group, a heptacenylene group, a pyranthrenylene group, an ovalenylene group, a carbazolylene group, a $C_1$-$C_{10}$alkyl carbazolylene group, a thienylene group, an indolylene group, a purinylene group, a benzimidazolylene group, a quinolinylene quinolylene group, a benzothiophenylene group, a parathiazinylene group, a pyrrolylene group, a pyrazolylene group, an imidazolylene group, an imidazolinylene group, an oxazolylene group, a thiazolylene group, a triazolylene group, a tetrazolylene group, an oxadiazolylene group, a pyridylene group, a pyridazinylene group, a pyrimidinylene group, a pyrazinylene group and a thianthrenylene group, a pyrrolidinylene group, a pyrazolidinylene group, an imidazolidinylene group, a piperidylene group, a piperazinylene group and a morpholinylene group.

7. The organic electroluminescent device of claim 1, wherein $Ar_3$, $Ar_4$, $Ar_5$ and $Ar_6$ are each independently selected from the group consisting of a phenyl group, a $C_1$-$C_{10}$ alkylphenyl group, a $C_1$-$C_{10}$ alkoxyphenyl group, a halophenyl group, a cyanophenyl group, a dicyanophenyl group, a trifluoromethoxyphenyl group, an o-, m-, or p-tolyl, an o-, m- or p-cumenyl group, a mesityl group, a phenoxyphenyl group, an (α,α-dimethylbenzene)phenyl group, a (N,N'-dimethyl)aminophenyl group, a (N,N'-diphenyl)aminophetryl group, a (N,N'-bis(methylphenyl)aminophenyl group, a (N,N'-dinaphthyl)aminophenyl group, a ($C_1$-$C_{10}$ alkylcyclohexyl)phenyl group, an (anthraceneyl)phenyl group, a biphenyl group, a $C_1$-$C_{10}$ alkylbiphenyl group, a $C_1$-$C_{10}$ alkoxybiphenyl group, a pentalenyl group, an indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group, a $C_1$-$C_{10}$ alkyl biphenylenyl group, a $C_1$-$C_{10}$ alkoxy biphenylenyl group, an anthr[acene]yl group, an azulenyl group, a heptalenyl group, an acenaphthalenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, a $C_{1-10}$ alkyl carbazolyl group, a thienyl group, an indolyl group, a purinyl group, a benzimidazolyl group, a quinolinyl group, a benzothlophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridyl group, a pyridazinyl group, a pyrimidinyl group, a pyrazinyl group and a thianthrenyl group(thianthrenyl), a pyrrolidinyl group, a pyrazolidinyl group, an imidazolidinyl group, a piperidinyl group, a piperazinyl group, a carbazolyl group, a benzoxazolyl group, a phenothiazinyl group, a 5H-dibenzoazepinyl group, a 5H-tribenzoazepinyl group and a morpholinyl group.

8. The organic electroluminescent device of claim 1, wherein $R_1$ is a substituted or unsubstituted cycloalkylene group, a substituted or unsubstituted cycloalkenylene group, or a substituted or unsubstituted cycloalkynylene group;

$Ar_1$ or $Ar_2$ is each independently selected from the group consisting of a phenylene group, a $C_1$-$C_{10}$ alkylphenylene group, a $C_1$-$C_{10}$ alkoxyphenylene group, a halophenylene group, a cyanophenylene group, a dicyanophenylene group, a trifluoromethoxyphenylene group, an o-, m-, or p-tolylene group, an o-, m- or p-cumenylene group, a mesitylene group, a phenoxyphenylene group, an (α,α-dimethylbenzene)phenylene group, a ($C_1$-$C_{10}$ alkylcyclohexyl)phenylene group, an (anthryl)phenylene group, a biphenylene group, a $C_1$-$C_{10}$ alkylbiphenylene group, a $C_1$-$C_{10}$ alkoxybiphenylene group, a pentalenyl group, an indenylene group, a naphthylene group, a $C_1$-$C_{10}$ alkylnaphthylene group, a $C_1$-$C_{10}$ alkoxynaphthylene group, a halonaphthylene group, a cyanonaphthylene group, a biphenylenylene group, a $C_1$-$C_{10}$ alkyl biphenylenylene group, a $C_1$-$C_{10}$alkoxy biphenylenylene group, a biphenylanthrylene group, an anthrylene group, an azulenylene group, a heptalenylene group, an acenaphthylenylene group, a phenanthrenylene group, a fluorenylene group, an anthraquinolylene group, a methylanthrylene group, a phenanthrylene group, a triphenylenylene group, a pyrenylene group, a chrysenylene group, an ethyl-chrysenylene group, a picenylene group, a perylenylene group, a chloroperylenylene group, a pentaphenylene group, a pentacenylene group, a tetraphenylene group, a hexaphenylene group, a hexacenylene group, a rubicenylene group, a coronenylene group, a trinaphtylenylene group, a heptaphenylene group, a heptacenylene group, a pyranthrenylene group, an ovalenylene group, a carbazolylene group, a $C_{1-10}$alkyl carbazolylene group, a thienylene group, an indolylene group, a purinylene group, a benzimidazolylene group, a quinolinylene quinolylene group, a benzothiophenylene group, a parathiazinylene group, a pyrrolylene group, a pyrazolylene group, an imidazolylene group, an imidazolinylene group, an oxazolylene group, a thiazolylene group, a triazolylene group, a tetrazolylene group, an oxadiazolylene group, a pyridylene group, a pyridazinylene group, a pyrimidinylene group, a pyrazinylene group and a thianthrenylene group, a pyrrolidinylene group, a pyrazolidinylene group, an imidazolidinylene group, a piperidylene group, a piperazinylene group and a morpholinylene group; and $Ar_3$, $Ar_4$, $Ar_5$ and $Ar_6$ are each independently selected from the group consisting of a phenyl group, a $C_1$-$C_{10}$ alkylphenyl group, a $C_1$-$C_{10}$ alkoxyphenyl group, a halophenyl group, a cyanophenyl group, a dicyanophenyl group, a trifluoromethoxyphenyl group, an o-, m-, or p-tolyl, an o-, m- or p-cumenyl group, a mesityl group, a phenoxyphenyl group, an (α,α-ditnethylhenzene)phenyl group, a (N,N'-dimethyl)aminophenyl group, a (N,N'-diphenyl)aminophenyl group, a (N,N'-bis(methylphenyl))aminophenyl group, a (N,N'-dinaptithyl)aminophenyl group, a ($C_1$-$C_{10}$ alkylcyclohexyl)phenyl group, an (anthraceneyl)phenyl group, a biphenyl group, a $C_1$-$C_{10}$ alkylbiphenyl group, a $C_1$-$C_{10}$ alkoxybiphenyl group, a pentalenyl group, an indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group, a $C_1$-$C_{10}$ alkyl biphenylenyl group, a $C_1$-$C_{10}$ alkoxy biphenylenyl group, an anthr[acene]yl group, an azulenyl group, a heptalenyl group, an acenaphthalenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a ruhicenyl group, a coronenyl group, a trinaphthylenyl group, a heptaphenyl group, a heptacenyl group, a pyranthrenyl group, an ovalenyl group, a carbazolyl group, a $C_1$-$C_{10}$ alkyl carbazolyl group, a thienyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridyl group, a pyridazinyl group, a pyrimidinyl group, a pyrazinyl group and a thianthrenyl group(thianthrenyl), a pyrrolidinyl group, a pyrazolidinyl group, an imidazolidinyl group, a piperidinyl group, a piperazinyl group, a carbazolyl group, a benzoxazolyl group, a phenothiazinyl group, a 5H-dibenzoazepinyl group, a 5H-tribenzoazepinyl group and a morpholinyl group.

9. The organic electroluminescent device of claim 1, being a compound represented by one of Formulae 2 through 16:

(2)

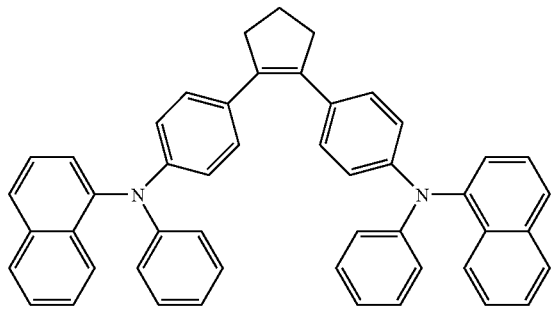

(3)

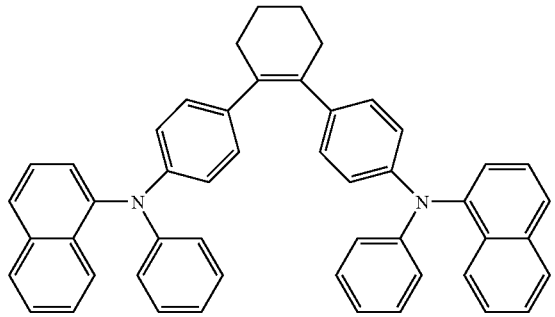

(4)

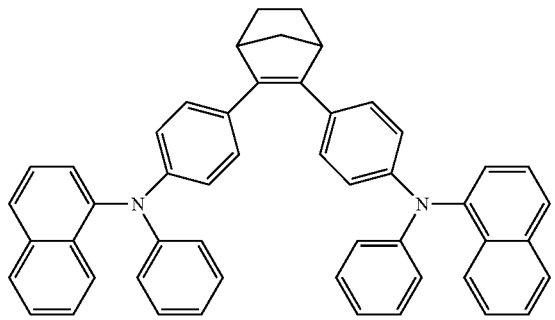

(5)

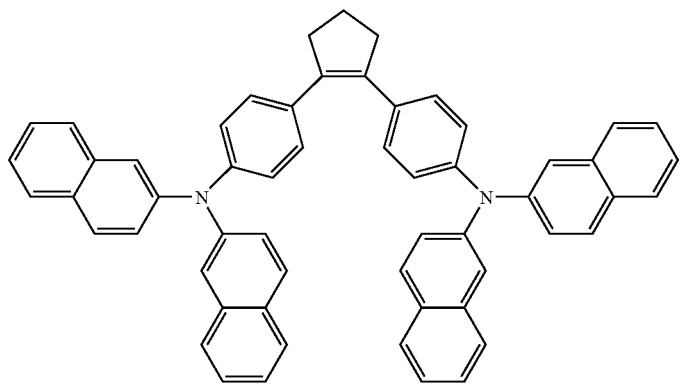

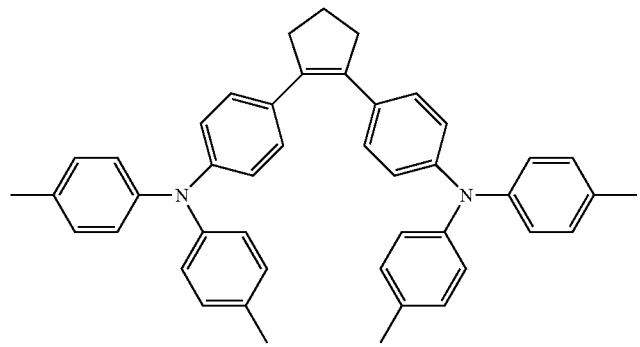
(6)
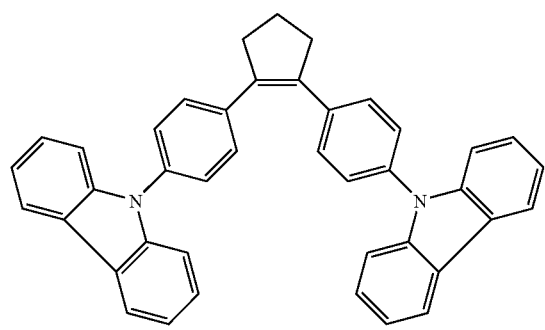
(7)
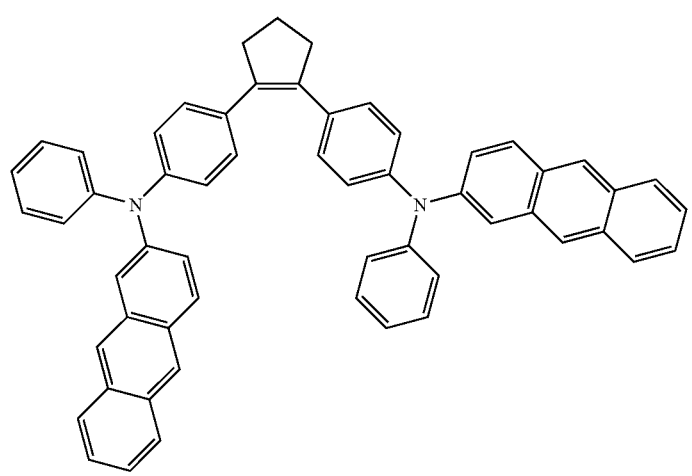
(8)
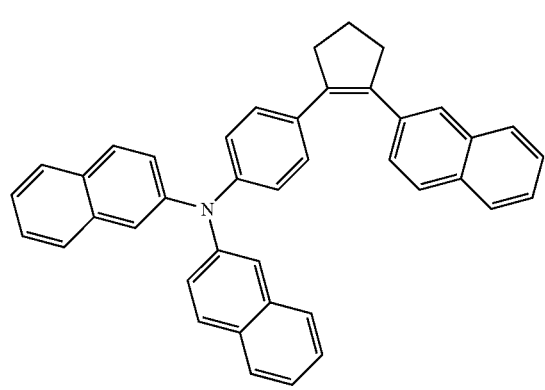
(9)

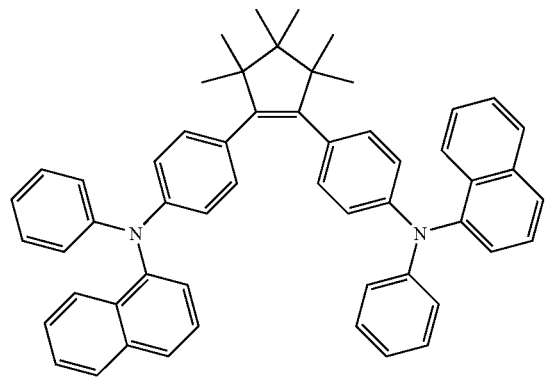
(10)
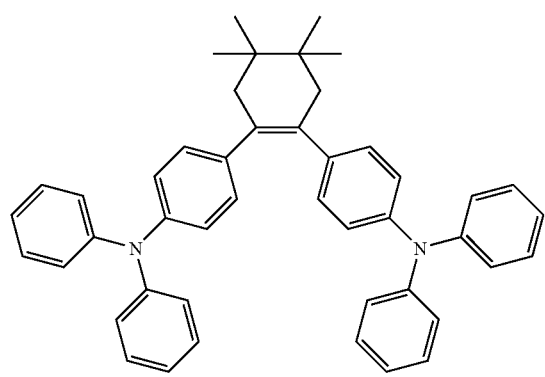
(11)
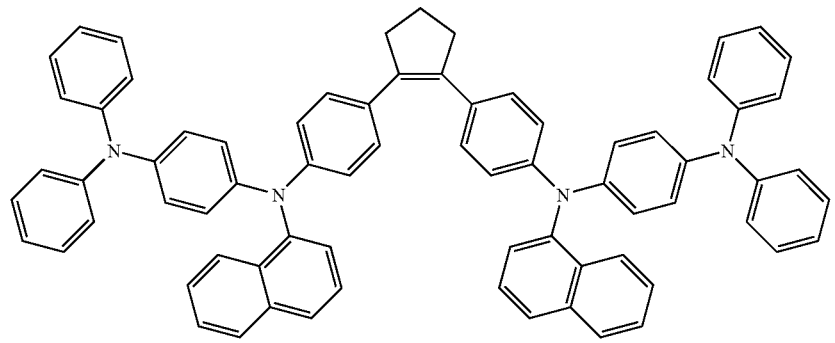
(12)
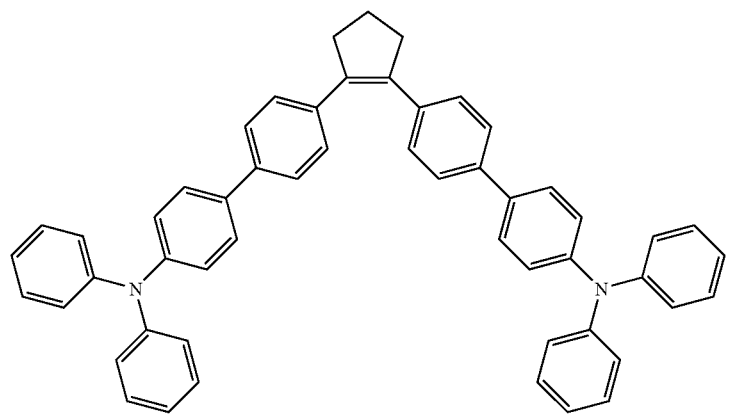
(13)

(14)

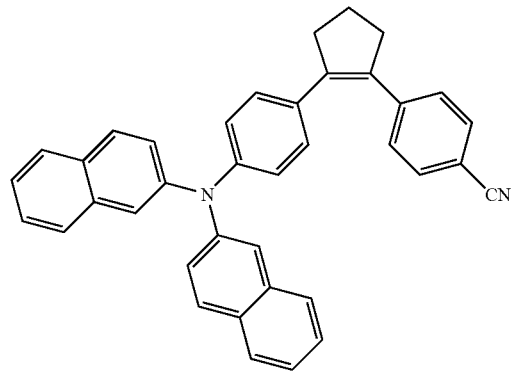

(15)

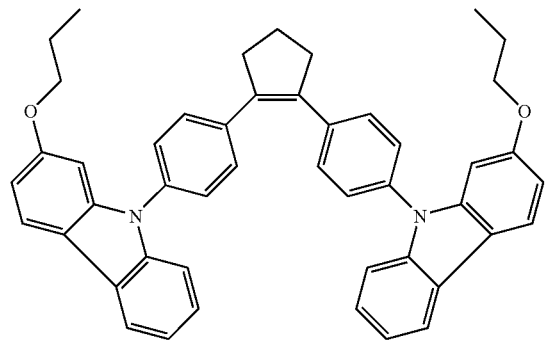

(16)

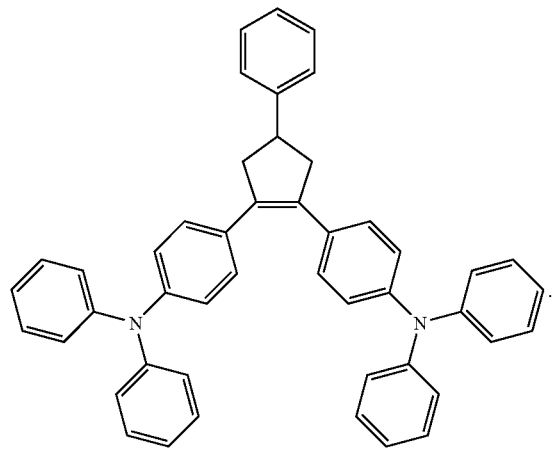

10. The organic EL device of claim 1, wherein the organic layer further comprises at least one layer selected from the group consisting of a hole injection layer, a hole transport layer, an electron blocking layer, a hole blocking layer, an electron transport layer, and an electron injection layer.

11. The organic EL device of claim 1, wherein the emissive layer further comprises a photoluminescent (PL) or fluorescent dopant of red, green, blue, or white.

12. The organic EL device of claim 11, wherein the photoluminescent dopant is an organic metal compound comprising at least one element selected from the group consisting of Ir, Pt, Os, Ti, Zr, Hf, Eu, Tb and Tm.

13. The organic EL device of claim 1, having a structure of the first electrode/a hole injection layer/the emissive layer/an electron transport layer/an electron injection layer/the second electrode, a structure of the first electrode/a hole injection layer/a hole transport layer/the emissive layer/an electron transport layer/an electron injection layer/the second electrode, or a structure of the first electrode/a hole injection layer/a hole transport layer/the emissive layer/a hole blocking layer/an electron transport layer/an electron injection layer/ the second electrode.

14. A method of manufacturing an organic electroluminescent (EL) device, comprising:
    forming a first electrode;
    forming an organic layer containing an organic light-emitting compound of a diarylethene derivative represented by Formula 1 on the first electrode; and forming a second electrode on the organic layer:

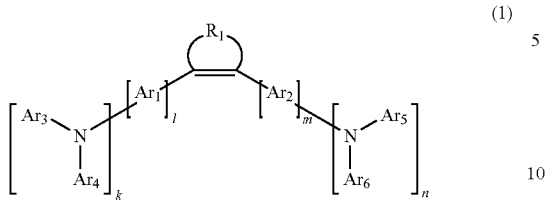

(1)

where $R_1$ is a substituted or unsubstituted $C_1$-$C_{30}$ alkylene group, an alkenylene group, or an alkynylene group;

$Ar_1$ and $Ar_2$ are each independently a substituted or unsubstituted $C_6$-$C_{30}$arylene group, or a substituted or unsubstituted $C_2$-$C_{30}$heteroarylene group;

$Ar_3$, $Ar_4$, $Ar_5$ and $Ar_6$ are each independently a substituted or unsubstituted $C_6$-$C_{30}$aryl group, or a substituted or unsubstituted $C_2$-$C_{30}$ heteroaryl group;

$Ar_3$ and $Ar_4$ can be linked to form a ring, and $Ar_5$ and $Ar_6$ can be linked to form a ring;

l and m are each independently integers form 1 to 6; and k and n are each independently integers from 0 to 6, wherein at least one of k and n is larger than or equal to 1.

15. The method of claim 14, wherein the organic layer is formed using a wet process selected from the group consisting of spin coating, inkjet printing, and spray printing, or a heat transfer method.

16. The method of claim 14, wherein the formation of the organic layer comprises depositing or coating the organic light-emitting compound on the first electrode and heat-treating the organic light-emitting compound.

17. The method of claim 14, wherein $R_1$ is a substituted or unsubstituted cycloalkylene group, a substituted or unsubstituted cycloalkenylene group, or a substituted or unsubstituted cycloalkynylene group;

$Ar_1$ or $Ar_2$ is each independently selected from the group consisting of a phenylene group, a $C_1$-$C_{10}$ alkylphenylene group, a $C_1$-$C_{10}$ alkoxyphenylene group, a halophenylene group, a cyanophenylene group, a dicyanophenylene group, a trifluorometboxyphenylene group, an o-, m-, or p-tolylene group, an o-, m- or p-cumenylene group, a mesitylene group, a phenoxyphenylene group, an (α,α-dimethylbenzene)phenylene group, a ($C_1$-$C_{10}$ alkylcyclohexyl)phenylene group, an (anthryl)phenylene group, a biphenylene group, a $C_1$-$C_{10}$ alkylbiphenylene group, a $C_1$-$C_{10}$ alkoxybipbenylene group, a pentalenyl group, an indenylene group, a naphthylene group, a $C_1$-$C_{10}$ alkylnaphthylene group, a $C_1$-$C_{10}$ alkoxynaphthylene group, a halonaphthylene group, a cyanonaphthylene group, a biphenylenylene group, a $C_1$-$C_{10}$ alkyl biphenylenylene group, a $C_1$-$C_{10}$alkoxy biphenylenylene group, a biphenylanthrylene group, an anthrylene group, an azulenylene group, a heptalenylene group, an acenaphthylenylene group, a phenanthrenylene group, a fluorenylene group, an anthraquinolylene group, a methylanthrylene group, a phenanthrylene group, a triphenylenylene group, a pyrenylene group, a chrysenylene group, an ethyl-chrysenylene group, a picenylene group, a perylenylene group, a chloroperylenylene group, a pentaphenylene group, a pentacenylene group, a tetraphenylenylene group, a hexaphenylene group, a hexacenylene group, a rubicenylene group, a coronenylene group, a trinaphthylenylene group, a heptaphenylene group, a heptacenylene group, a pyranthrenylene group, an ovalenylene group, a carbazolylene group, a $C_{1-10}$alkyl carbazolylene group, a thienylene group, an indolylene group, a purinylene group, a benzimidazolylene group, a quinolinylene quinolylene group, a benzothiophenylene group, a parathiazinylene group, a pyrrolylene group, a pyrazolylene group, an imidazolylene group, an imidazolinylene group, an oxazolylene group, a thiazolylene group, a triazolylene group, a tetrazolylene group, an oxadiazolylene group, a pyridylene group, a pyridazinylene group, a pyrimidinylene group, a pyrazinylene group and a thianthrenylene group, a pyrrolidinylene group, a pyrazolidinylene group, an imidazolidinylene group, a piperidylene group, a piperazinylene group and a morpholinylene group; and $Ar_3$, $Ar_4$, $Ar_5$ and $Ar_6$ are each independently selected from the group consisting of a phenyl group, a $C_1$-$C_{10}$ alkylphenyl group, a $C_1$-$C_{10}$ alkoxyphenyl group, a halophenyl group, a cyanophenyl group, a dicyanophenyl group, a trifluoramethoxyphenyl group, an o-, m-, or p-tolyl, an o-, m- or p-cumenyl group, a mesityl group, a phenoxyphenyl group, an (α,α-dimethylbenzene)phenyl group, a (N,N'-dimethyl)aminophenyl group, a (N,N'-diphenyl)aminophenyl group, a (N,N'-bis(methylphenyl)) aminophenyl group, a (N,N'-dinaphthyl)aminophenyl group, a ($C_1$-$C_{10}$ alkylcyclohexyl)phenyl group, an (anthraceneyl)phenyl group, a biphenyl group, a $C_1$-$C_{10}$ alkylbiphenyl group, a $C_1$-$C_{10}$ alkoxybiphenyl group, a pentalenyl group, an indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group, a $C_1$-$C_{10}$ alkyl biphenylenyl group, a $C_1$-$C_{10}$ alkoxy biphenylenyl group, an anthr[acene]yl group, an azulenyl group, a heptalenyl group, an acenaphthalenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, to heptacenyl group, a pyranthrenyl group, an ovalenyl group, a carbazolyl group, a $C_1$-$C_{10}$ alkyl carbazolyl group, a thienyl group, an indolyl group, a purinyl group, a benzimidazolyl group, a quinolinyl group, a benzothiophenyl group, a parathiazinyl group, to pyrrolyl group, a pyrazolyl group, an imidazolyl group, an imidazolinyl group, an oxazolyl group, a thiazolyl group, a triazolyl group, a tetrazolyl group, an oxadiazolyl group, a pyridyl group, a pyridazinyl group, a pyrimidinyl group, a pyrazinyl group and a thianthrenyl group(thianthrenyl), a pyrrolidinyl group, a pyrazolidinyl group, an imidazolidinyl group, a piperidinyl group, a piperazinyl group, a carbazolyl group, a benzoxazolyl group, a phenothiazinyl group, a 5H-dibenzoazepinyl group, as 5H-tribenzoazepinyl group and a morpholinyl group.

18. The organic electroluminescent device manufactured by the method of claim 14.

* * * * *